United States Patent
Spivak et al.

(10) Patent No.: US 7,803,955 B2
(45) Date of Patent: Sep. 28, 2010

(54) METHOD FOR PREPARING 2,5,7,8-TETRAMETHYL-2-(2'-CARBOXYETHYL)-6-ACETOXYCHROMAN-PRECURSOR-α-CEHC PRECURSOR

(75) Inventors: Anna Yulievna Spivak, Ufa (RU); Viktor Nikolaevich Odinokov, Ufa (RU); Oxana Valerievna Knyshenko, Ufa (RU)

(73) Assignee: Institut Neftekhimii I Kataliza Ran, Bashkortostan (RU)

( * ) Notice: Subject to any disclaimer, the term of this patent is extended or adjusted under 35 U.S.C. 154(b) by 0 days.

(21) Appl. No.: 11/921,248

(22) PCT Filed: Jun. 15, 2006

(86) PCT No.: PCT/RU2006/000309

§ 371 (c)(1),
(2), (4) Date: Jun. 22, 2009

(87) PCT Pub. No.: WO2006/135278

PCT Pub. Date: Dec. 21, 2006

(65) Prior Publication Data

US 2009/0306413 A1    Dec. 10, 2009

(30) Foreign Application Priority Data

Jun. 16, 2005   (RU) .............................. 2005118733

(51) Int. Cl.
*C07D 311/58* (2006.01)
(52) U.S. Cl. ..................................................... 549/410
(58) Field of Classification Search ................... 549/410
See application file for complete search history.

(56) References Cited

FOREIGN PATENT DOCUMENTS

| JP | 42013780 | 8/1967 |
|---|---|---|
| JP | 47014568 | 5/1972 |
| RU | 2001106184 | 2/2003 |

OTHER PUBLICATIONS

Odinokov et al., Russian Chemical Bulletin, (2001), 50(11), 2227-2230.*
Kantoci, D., et al. "Endogenous natriuretic factors 6: the stereochemistry of a natriuretic gamma-tocopherol metabolite LLU-alpha." *J Pharmacol Exp Ther* (1997) vol. 282, pp. 648-656.
Pope, S. A. S., et al. "Synthesis and Analysis of Conjugates of the Major Vitamin E Metabolite, α-CEHC." *Free Radical Biology & Medicine* (2002) vol. 33, No. 6, pp. 807-817.
Weichet, J., et al. "Collection of Czechoslovak Chemical Communications" (1959) vol. 24 pp. 1689-1694.
Mayer, O., et al. "Synthesis of Vitamin E, Methods of Enzymology." *Vitamins and Coenzymes Part C*, Academy Press, NY (1971) vol. XVIII 273-275.
English abstract of JP 42013780 dated Aug. 4, 1967.
English abstract of JP 47014568 dated May 1, 1972.
English translation of abstract and claims of RU 2001106184 dated Feb. 10, 2003.
Brigelius-Flohe, R., et al. "The European perspective on vitamin E: current knowledge and future research." *American Journal of Clinical Nutrition* (2002) vol. 76, No. 4, pp. 703-716.
Hensley, K., et al. "New Perspectives on Virtamin E:γ-Tocopherol and Carboxyethylhydroxychroman Metabolites in Biology and Medicine." *Free Radical Biology and Medicine* (2004) vol. 36, No. 1, pp. 1-15.
Berezovsky, V. M. "Vitamin Chemistry." *Pishchevaya Premyshlennost* (1973) p. 286.
Schultz, M., et al. "Novel urinary metabolite of alpha-tocopherol, 2,5,7,8-tetramethyl-2 (2'-carboxyethyl)-6-hydroxychroman, as an indicator of an adequate vitamin E supply?."*Am. J Clin Nutr.* (1995) vol. 62 pp. 1527S-1534S (Abstract).
Murray, Jr., E., et al. "Endogenous natriuretic fa tors 3: isolation and characterization of human natriuretic factors LLU-alpha, LLU-beta 1, and LLU-gamma." *Life Sci.* (1995) vol. 5, pp. 2145-2161.
Wechter, W. J., et al. "A new endogenous natriuretic factor: LLU-alpha." *Proc Ntl Acad Sci U S A* (1996) vol. 93, pp. 6002-6007.
Betancor-Fernandez, A., et al. "In vitro antioxidant activity of 2,5,7,8-tetramethyl-2(2'carboxyethyl)-6-hydroxychroman (aplha-CEHC), a virtamin E metabolite." *Free Radic Res.* (2002) vol. 36, No. 8, pp. 915-921 (Abstract).
Yoshida, Y., et al. "Antioxidant effects of alpha- and gamma-carboxyethyl-6-hydroxychromans."*Biofactors* (2002) vol. 16, No. 3-4, pp. 93-103 (Abstract).

* cited by examiner

*Primary Examiner*—Janet L Andres
*Assistant Examiner*—David E. Gallis
(74) *Attorney, Agent, or Firm*—Ladas and Parry LLP

(57) ABSTRACT

The contemplated invention relates to the field of synthesis of biologically active substances, namely to the synthesis of an acetate derivative of the main water-soluble α-tocopherol metabolite known under the name of α-CEHC, which is prepared by the acid-catalyzed reaction of condensation of trimethyl hydroquinone with linalool in boiling octane, using n-toluenesulfonic acid or (+)-camphor-10-sulfonic acid as the catalyst. The reaction is carried out for 3 hours at the trimethyl hydroquinone:linalool:catalyst mole ratio of 1:1:0.1. The forming product is acetylated with acetic anhydride in pyridine at room temperature for 0.5 hour, and then ozonized in acetone in the presence of $Ba(OH)_2$, oxidized with Jones' reagent in acetone, and isolated on silica gel column chromatography.

Said compound is an acetate derivative of the main α-tocopherol metabolite—α-CEHC, for which high efficiency has been noted in treating disorders of the central nervous system.

4 Claims, No Drawings

METHOD FOR PREPARING 2,5,7,8-TETRAMETHYL-2-(2'-CARBOXYETHYL)-6-ACETOXYCHROMAN-PRECURSOR-α-CEHC PRECURSOR

FIELD OF THE ART

The contemplated invention relates to the synthesis of biologically active substances, particularly of 2,5,7,8-tetramethyl-2-(2'-carboxyethyl)-6-acetoxychroman, which is a precursor of the main water-soluble metabolite of α-tocopherol, 2,5,7,8-tetramethyl-2-(2'-carboxyethyl)-6-hydroxychroman (α-CEHC).

PRIOR ART

α-Tocopherol (vitamin E) (I) is a known natural antioxidant protecting lipids from peroxidation. In the last decade other vitally important functions of α-tocopherol have been found. α-Tocopherol determines the activity of protein kinase C (an enzyme responsible for the phosphorylation of membrane proteins), modulates the proliferation of vascular cells of smooth muscles and promotes accumulation of α-tropomyosin muscular fibers (R. Brigelius-Flohe et al. The European perspective on vitamin E: current knowledge and future research, *Am. J Clin. Nutr.* 2002, 76, No. 4, pp. 703-716).

One of the main factors defining the biology of α-tocopherol is metabolic conversion of the side wicking chain that affects 2'-, 4'- and 8'-carbon atoms. Undeniable facts have been accumulated, from which it follows that in the process of natural metabolism the side wicking chain of α-tocopherol undergoes ω-oxidation, catalyzed by cytochrome-dependent enzyme P450, followed by oxidative cleavage. This process on the main proceeds in the liver and leads to water-soluble glucoronide and sulfate conjugates of 2,5,7,8-tetramethyl-2-(2'-carboxyethyl)-6-hydroxychroman, known under the name of α-CEHC (II). (K. Hensley et al., New perspectives on vitamin E: γ-tocopherol and carboxyethylhy-doxychroman metabolites in biology and medicine, *Free Radical Biol. Med.*, 2004, vol. 36, No. 1, pp. 1-15).

The presence of hydroxyl group in the $6^{th}$ position of the chroman fragment of tocopherol and its analogs is necessary for the manifestation of their biological activity. At the same time, some chromanol esters, including acetates, display a higher biological activity than free chromanols do. For instance, the vitamin activity of α-tocopheryl acetate is 1.47 times higher than the activity of non-acetylated α-tocopherol. Acetate derivatives of chromanols are more resistant to oxidation, they are more easily assimilated by the organism and are easily hydrolyzable (V. M. Berezovsky, Vitamin Chemistry. Moscow. 'Pishchevaya Promyshlennost'. 1973, p. 286).

Studies in α-tocopherol metabolism are extremely useful for the determination of its function in vivo, and acid (II) and its esters are a suitable biomarker for determining the status of vitamin E, because excretion of the conjugates of acid (II) grows with an increase of α-tocopherol consumption after exceedance of its threshold concentration in blood plasma (M. Schultz et al., Novel urinary metabolite of α-tocopherol, 2,5,7,8-tetramethyl-2-(2'-carboxyethyl)-6-hydroxychroman, as an indicator of an adequate vitamin E supply, *Am. J. Clin. Nutr.* 1995, vol. 62, pp.; 1527S -1534S).

Preparations based on α-CEHC metabolite (II) and its analog synthesized from γ-tocopherol (γ-CEHC) differ essentially in their biological activity from their tocopherol precursors. The activity of these acids is not associated directly with their antioxidant properties. To a greater extent they produce anti-inflammatory, antitumoric and natriuretic effect based on their interaction with proteins as endogenous ligands. Recently γ-CEHC (also known under the name LLU-α) was identified as an endogenous natriuretic factor in patients with uremia (Jr. E. D. Murray et al. Endogenous natriuretic factors 6: isolation and characterisation, *Life Sci.* 1995, 5, 2145-2161). Unlike the known diuretics, it exclusively selectively promotes the excretion of sodium ions without affecting potassium ions (W. J. Wecher et al., A new endogenous natriuretic factor: LLU-alpha, *Proc. Natl. Acad. Sci. USA,* 1996, 93, pp. 6002-6007).

The high efficiency of α-CEHC and γ-CEHC metabolites as compared with classical medicinal preparations was noted in treating such disorders of the central nervous system as Alzheimer's disease, Parkinson's disease, etc. (Hinsley K. et al., *Free Radical Biol. Med.*, 2004, vol. 36, No. 1, pp. 1-15).

Scheme 1

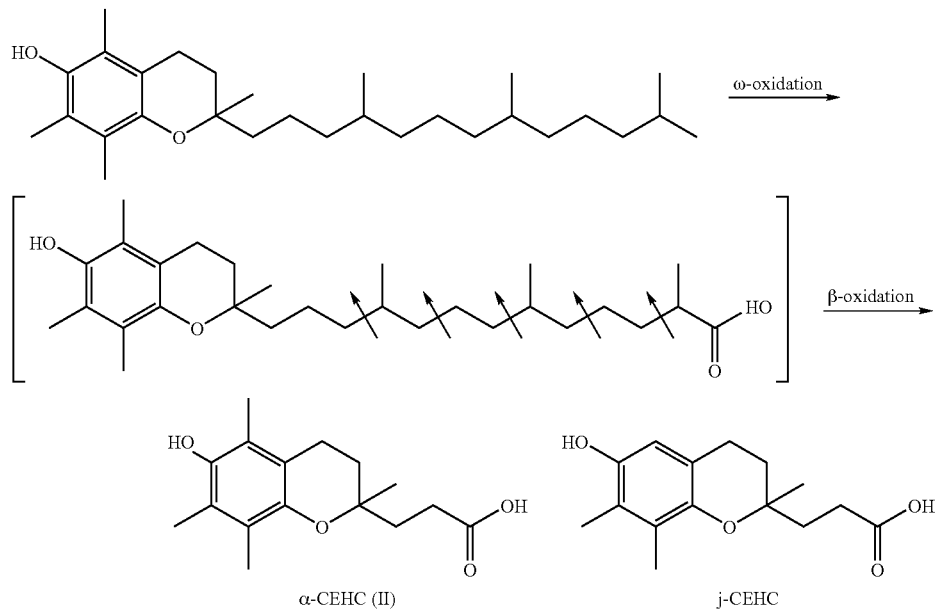

Investigations of the antioxidant activity of the acid (II) in vitro in various model oxidative reactions have shown its high antioxidant properties comparable with such known preparations as α-tocopherol, ascorbic acid, and the cardioprotective agent Trolox, a short-chain analog of α-tocopherol (A. Betancor-Fernandez et al., In vitro antioxidant activity of 2,5,7,8-tetramethyl-2-(2'-carboxyethyl)-6-hydroxychroman (alpha-CEHC), a vitamin E metabolite, *Free Radic. Res.,* 2002, 36, No. 8, pp. 915-921; Y. Yoshida, E. Niki, Antioxidant effect of alpha- and gamma-carboethyl-6-hydroxychromans, *Biofactors,* 2002, vol, 16, No. 3-4, pp. 93-103).

In spite of the found unique properties of the acid (II) and the opening prospects of its use in biology and medicine, the methods of synthesizing this compound are very limited.

Known in the art is a method of preparing the acid (II) and its precursor 2,5,7,8-tetramethyl-2-(2'-carboxyethyl)-6-acetoxychroman (V), based on the reaction of condensation of trimethyl hydroquinone (TMHQ) (III) with γ-methyl-γ-vinylbutyrolactone (IV), which was carried out in dioxane in the presence of boron trifluoride etherate (D. Kantoci et al., Endogenous natriuretic factors 6: the stereochemistry of a natriuretic gamma-tocopherol metabolite LLU-alpha, *J Pharmacol. Exp. Ther.* 1997, 282, pp. 648-656; S. A. S. Pope et al., Synthesis and analysis of conjugates of the major vitamin E metabolite, α-CEHC, *Free Radical Biol. Med.,* 2002, vol. 33, No. 6, pp. 807-817) or in a mixture of acetic acid and acetic anhydride under the action of a mixture of $ZnCl_2$ and $BF_3 \cdot OEt_2$. Subsequent hydrolysis of the acetate protection in the chroman (V) led to the acid (II) (J. Weichet et al., *Collection Czech. Chem. Commun.,* 1959, vol. 24, pp. 1689-1694; H. Mayer, O. Isler, Synthesis of vitamin E, Methods in Enzymology, vol. XVIII. Vitamin and Coenzymes. Part C. *Academ. Press,* 1971, p. 274).

The intermediate lactone (IV) was prepared by condensation of vinyl magnesium bromide with ethyl levulinate (VI) or by the reaction of levulinic acid (VII) with sodium acetylinide in liquid ammonia followed by partial hydrogenation of the athenyl group in the intermediate γ-lactone (VIII).

As can be seen, the known methods of the synthesis of the acetate derivative of the acid (II)—2,5,7,8-tetramethyl-2-(2'-carboxyethyl)-6-acetoxychroman (V), presented in Scheme 2, contemplate preliminary preparation in several steps of γ-methyl-γ-vinyl butyrolactone (IV). They have the following disadvantages: the γ-methyl-γ-vinyl butyrolactone (IV) is not a vendible product; and it is prepared in two steps from ethyl levulinate (VI) or in three steps from levulinic acid (VII), by using fire- and explosion-hazardous sodium acetylinide or a Grignard reagent. The condensation reaction is low-adaptable to stream-lined production methods, since it proceeds under the action of condensing agents highly sensitive to the humidity of air. When preparing lactone (IV) and carrying out the reaction of condensation of the lactone (IV) with TMHQ (III), it is necessary to use dry solvents and inert atmosphere.

ESSENCE OF THE INVENTION

The authors propose a new method for preparing an acetate derivative of the acid (II)—2,5,7,8-tetramethyl-2-(2'-carboxyethyl)-6-acetoxychroman (V), consisting in carrying out the reaction of condensation of TMHQ (II) with linalool (IX) in boiling octane under the action of catalysts: n-TsOH or (+)-camphor-10-sulfonic acid (CSA), followed by treating the product of condensation with acetic anhydride in pyridine at room temperature. The reaction of condensation leads to 2,5,7,8-tetramethyl-2-(4-methyl-3-penten-1-yl)-6-acetoxychroman with selectivity of 68% and 75% (n-TsOH and CSA catalysis, respectively). Ozonolysis of the 2,5,7,8-tetram- Scheme 2

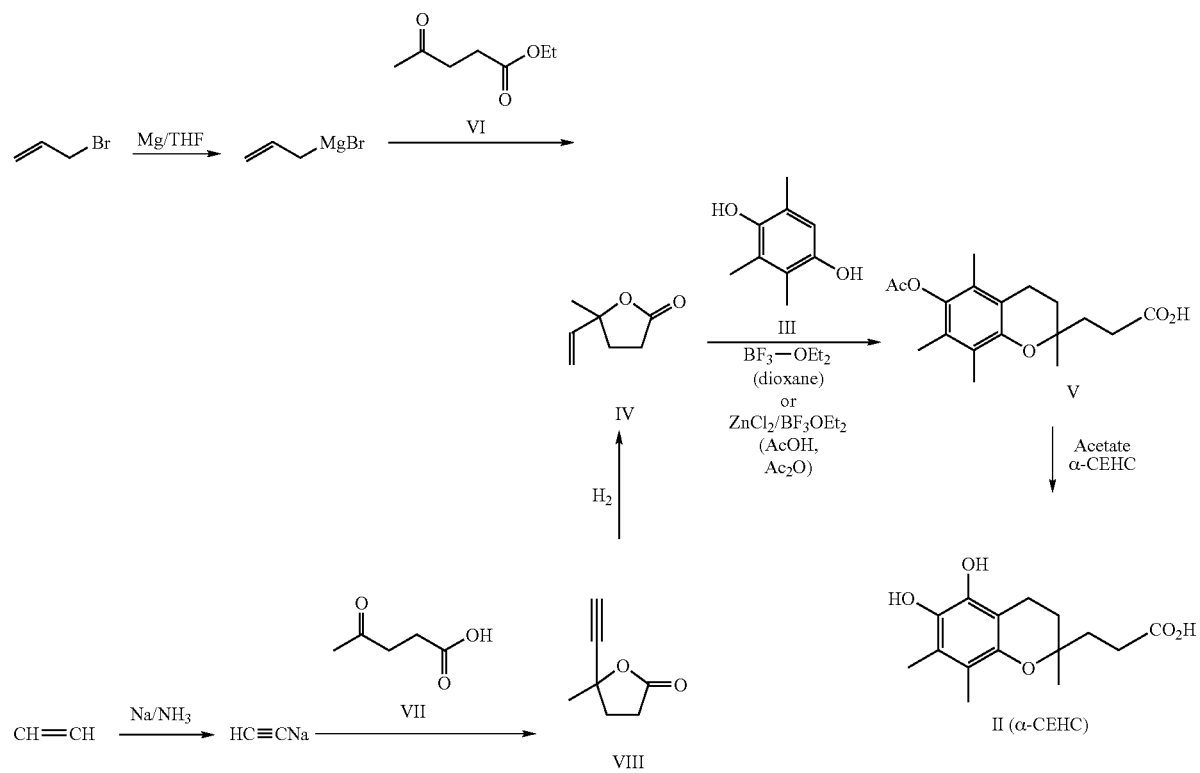

ethyl-2-(4-methyl-3-penten-1-yl)-6-acetoxychroman (X) in acetone in the presence of Ba(OH)$_2$ at room temperature and subsequent oxidation of the forming aldehyde with Jones' reagent in acetone at room temperature lead to the target acetate derivative of α-CEHC-2,5,7,8-tetramethyl-2-(2'-carboxyethyl)-6-acetoxychroman (V). The yield of 2,5,7,8-tetramethyl-2-(2'carboxyethyl)-6-acetoxychroman (V) as calculated for linalool (X) is 28-29% (Scheme 3).

2,5,7,8-Tetramethyl-2-(2'-carboxyethyl)-6-hydroxychroman (α-CEHC) (II) when necessary can be easily prepared by the hydrolysis of 2,5,7,8-tetramethyl-2-(2'carboxyethyl)-6-acetoxychroman (V) according to the known method (J. Weichet et al., *Collection Czech. Chem. Comnmun.* 1959, vol. 24, pp. 1689-1694).

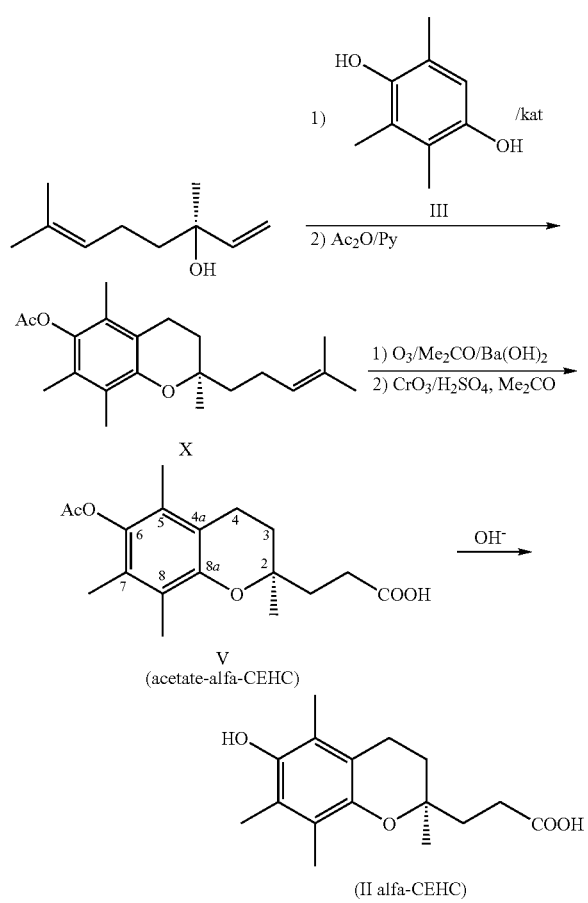

Scheme 3

ADVANTAGES OF THE PROPOSED METHOD

1. In the reaction of condensation an easily available vinyl carbinol, linalool, is used.
2. As the catalysts stable sulfonic acids (n-TsOH and CSA) are used, working with which in contrast to the catalysts employed earlier (ZnCl$_2$ and BF$_3$ OEt$_2$) does not require specific conditions (absence of humidity, inert atmosphere).
3. Besides the reaction of condensation the proposed scheme of the synthesis of the acetate derivative (α-CEHC) (V) comprises reactions of the acetate protection of phenolic hydroxyl, ozonolysis and oxidation, which are carried out by following typical, non-laborious techniques and proceed selectively with a high yield of the required products.

The end product—2,5,7,8-tetramethyl-2-(2'-carboxyethyl)-6-acetoxychroman (V) can be easily purified by column chromatography on silica gel from mirror impurities formed in the reaction of condensation of TMHQ (III) with linalool (IX).

The invention is further illustrated by the following examples which disclose preferable embodiments of the invention and cannot be regarded as limiting the scope of claims of the invention.

EXAMPLE 1

Preparation of 2,5,7,8-tetramethyl-2-(2'-carboxyethyl)-6-acetoxychroman (V)

To a boiling suspension of 0.4 g (2.6 mmol) of TMHQ (III) and 0.061 g (0.26 mmol) of the CSA catalyst in 3 ml of n-octane while boiling 0.40 g (2.6 mmol) of vinyl-carbinol (IX) were slowly added. The reaction mixture was boiled for 3 hours, then cooled down to room temperature and poured into a saturated solution of NaHCO$_3$ (30 ml). The product was extracted with EtOAc, the organic layers were washed with a saturated NaCl solution and dried over MgSO$_4$. The filtrate was evaporated and the residue was chroma-tographed on a column with SiO$_2$ (16 g). By elution with n-hexane a fraction (R$_f$ 0.9, n-hexane EtOAc, 1:1) of non-polar substances was isolated, then with a mixture (10:1) of n-hexane/EtOAc a fraction (R$_f$ 0.7, n-hexane—EtOAc, 1:1) was eluted, by the evaporation of which 0.57 g of an oil-like substance was obtained, which was dissolved in 5.6 ml of dry pyridine; 4.3 ml of acetic anhydride were added with stirring, the contents were kept for 0.5 h at room temperature, then poured into 15 ml of ice water, extracted with EtOAc, washed successively with a 3M solution of HCl, a saturated solution of NaHCO$_3$, H$_2$O, and dried with MgSO$_4$. After evaporation 0.63 g of a product was obtained, containing, according to GLC data, 75% acetate X, or 0.47 g (1.4 mmol), which was dissolved in 6 ml of acetone, then 0.6 g (3.5 mmol) of Ba(OH)$_2$, 0.15 ml of H$_2$O were added, and at room temperature an ozone-oxygen mixture was passed with a velocity of 30 lit-h$^{-1}$ for 9 min (1.5 mmol of O$_3$ with the ozonator capacity of 10 mmol of O$_3$-h$^{-1}$), whereafter the reaction mixture was filtered off and the filtrate was evaporated in vacuum. The obtained product was dissolved in 15 ml of EtO$_2$, dried with MgSO$_4$, evaporated, the residue (0.54 g) was dissolved in 4 ml of acetone, the solution was cooled with ice, and 1 ml of Jones' reagent prepared from 1.33 g of CrO$_3$, 3.8 ml of H$_2$O and 1.2 ml of H$_2$SO$_4$ was added dropwise with intensive stirring.

There was observed stratification of the reaction mixture into a lower green-colored layer of chromium salts and an upper layer containing the reaction products dissolved in acetone. The mixture was stirred for 2 h at room temperature, extracted with EtOAc (15 ml), the organic layer was washed with a saturated solution of NaCl and dried with MgSO$_4$. The residue after evaporation was chromatographed on a column with SiO$_2$ (6 g). By elution with a mixture (5:1) of n-hexane/EtOAc a fraction (R$_f$ 0.7, n-hexane-EtOAc, 1:1) was isolated, containing minor impurities forming in the reaction of condensation of TMHQ (III) with vinylcarbinol (IX). Then by using elution with methanol a fraction with R$_f$ 0.5 (CHCl$_3$-MeOH 1:1) was obtained, the evaporation of which gave 0.24 g (29% as calculated for vinylcarbinol (IX) of 2,5,7,8-tetramethyl-2-(2'-carboxyethyl)-6-acetoxychroman (V), m.p. 149-150° C. (compare: Weichet et al., *Collection Czech. Chem. Commun.*, 1959, vol. 24, pp. 1689-1694).

IR spectrum, v/cm-$^{-1}$: 1210, 1080 (C—O) 1730 (C=O), 3200-3500 (CH).

UV spectrum (MeOH), $\lambda_{max}$/nm ($\epsilon$): 278(1415); 284(1489).

$^1$H NMR spectrum ($\delta$ ppm, J/Hz): 1.21 (s, 3H, 3H,Me); 1.79-2.20 (m, 4H, H(3), H(1'), 1.94, 1.97, 2.06 (s, 9H, Ar-Me), 2.28 (s, 3H, MeCO$_2$); 2.50-2.75 (m, 4H, H(4), H(2')).

$^{13}$C NMR spectrum ($\delta$ppm): 12.06; 12.25; 13.12 (Ar-Me); 20.50 (MeCO); 21.43 (C(4)); 24.02 (MeC(2); 29.51 (C(2')); 32.26 (C(3)); 36.96 (C(1')); 75.78 (C(2)); 118.70; 123.75; 126.11; 127.65; (C(4a)); (C(5)); (C(7)); (C(8)); 141.97; (C(8a)); 150.26; (C(6)); 171.69 (Me$\underline{C}$O); 183.05 ($\underline{C}$O$_2$H).

EXAMPLE 2

From 4.0 g (26 mmol) of TMHQ (III), 4.01 g (26 mmol) of (IX) and 0.45 g (2.6 mmol) of n-TsOH under the conditions described in Example 1 there were obtained 5.3 g of product which was dissolved in 52 ml of dry Py, 40.2 ml of acetic anhydride were added under stirring, kept for 0.5 h at room temperature, then poured into 120 ml of ice water, extracted with EtOAc, washed with a 3N solution of HCl, with a saturated solution of NaHCO$_3$, H$_2$O, dried with MgSO$_4$, having obtained 5.9 g of an oil-like substance containing, according to the GLC data, 68% or 4.01 g (12.1 mmol) of the acetate (X), which substance was dissolved in 60 ml of acetone, 15.12 g (29.9 mmol) of Ba(OH)$_2$, 1.5 ml of H$_2$O were added, and at room temperature an ozone-oxygen mixture was passed with a velocity of 30 lit·h$^{-1}$ for 75 min (12.5 mmol of O$_3$ with the ozonator capacity of 10 mmol of O$_3$·h$^{-1}$), whereafter the reaction mixture was filtered off and the filtrate was evaporated at a reduced pressure.

The obtained product was dissolved in 100 ml of Et$_2$O, dried with MgSO$_4$, evaporated. The residue (5.2 g) was dissolved in 40 ml of acetone, cooled with ice, and 7 ml of Jones' reagent prepared from 2.66 g of CrO$_3$, 7.6 ml of H$_2$O and 2.4 ml of H$_2$SO$_4$ was added dropwise with intensive stirring. There was observed stratification of the reaction mixture into a lower green-colored layer of chromium salts and an upper layer containing the reaction products dissolved in acetone. The mixture was stirred for 2 h at room temperature, extracted with EtOAc. The mixture was stirred for 2 h at room temperature, extracted with EtOAc, the organic layers were washed with a saturated solution of NaCl and dried with MgSO$_4$. The filtrate was evaporated and the residue was chromatographed on a column with SiO$_2$, as described in Example 1. There was obtained a fraction with R$_f$ 0.5 (CHCl$_3$-MeOH, 1:1), the evaporation of which gave 2.3 g (28% as calculated for vinylcarbonyl (IX) of 2,5,7,8-tetramethyl-2-(2'-carboxyethyl)-6-acetoxychroman (V); the $^1$H and $^{13}$C NMR spectra are identical with the spectra presented in Example 1.

The invention claimed is:

1. A method for preparing a precursor of α-CEHC, 2,5,7,8-tetramethyl-2-(2'-carboxyethyl) -6-acetoxychroman, which comprises the following steps:
    a) carrying out an acid-catalyzed reaction of condensation of trimethyl hydroquinone with linalool in boiling n-octane;
    b) treating the product obtained in step a) in said condensation reaction with acetic anhydride in pyridine;
    c) ozonizing the product from step b) in the presence of Ba(OH)$_2$ in acetone at room temperature;
    d) oxidizing the product from step c) in the same solvent with Jones' reagent (CrO$_3$/H$_2$SO$_4$);
    e) isolating the target product by column chromatography.

2. The method of claim 1, wherein the acids catalyzing said condensation reaction are n-toluenesulfonic acid or (+)-camphor-10-sulfonic acid.

3. The method of claim 1, wherein the trimethyl hydroquinone:linalool:catalyst mole ratio is 1:1:0.1.

4. The method of claim 1, wherein the column chromatography is silica gel chromatography.

* * * * *